(12) United States Patent
Firestone et al.

(10) Patent No.: US 6,855,689 B2
(45) Date of Patent: Feb. 15, 2005

(54) ENZYME-ACTIVATED ANTI-TUMOR PRODRUG COMPOUNDS

(75) Inventors: Raymond A. Firestone, Stamford, CT (US); Leila A. Telan, Somerville, MA (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 84 days.

(21) Appl. No.: 10/154,507

(22) Filed: May 23, 2002

(65) Prior Publication Data

US 2002/0147138 A1 Oct. 10, 2002

Related U.S. Application Data

(62) Division of application No. 09/551,147, filed on Apr. 15, 2000, now abandoned.
(60) Provisional application No. 60/134,135, filed on May 14, 1999.

(51) Int. Cl.$^7$ ........................... A61K 38/00; C07K 5/00
(52) U.S. Cl. ........................... 514/2; 530/300; 530/402; 435/23; 435/218; 435/226; 424/1.53; 424/9.1; 424/193.1
(58) Field of Search ..................... 435/23, 218, 226; 514/2; 530/300, 402; 424/1.53, 193.1, 9.1

(56) References Cited

U.S. PATENT DOCUMENTS 4,703,107 A    10/1987    Monsigny et al.

FOREIGN PATENT DOCUMENTS

| EP | 0 255 341 | 2/1988 |
| EP | 0 624 377 | 11/1994 |
| WO | WO 97/12624 | 4/1997 |
| WO | WO 97/14416 | 4/1997 |
| WO | WO 97/45117 | 12/1997 |
| WO | WO 98/04277 | 2/1998 |
| WO | WO 98/13059 | 4/1998 |
| WO | WO 00/33888 | 6/2000 |
| WO | WO 00/64486 | 11/2000 |

OTHER PUBLICATIONS

Hilpert et al., Characterization and Optimizing Protease/Peptide Inhibitor Interactions, a New Application for Spot Synthesis. J. Biochem. 128, 1051–1057 (2000).*

Intll Search Report for PCT/US00/10327.

Park, John E. et al; Fibroblast Activation Protein, a Dual Specificity Serine Protease Expressed in Reactive Human Tumor Stromal Fibroblasts, Journal of Biological Chemistry, Dec. 17, 1999, pp. 36505–36512, vol. 274, No. 51.

Calieti, P. et al; Preparation and Properties of Monomethoxy Poly(Ethylene Glycol) Doxorubicin Conjugates Linked by an Amino Acid or a Peptide as Spacer, 2193 II Farmaco, 48 (1993) Jul., No. 7, Rom, It. pp 919–932.

International Search Report–PCT/EP 00/04261.

Starcher, Barry et al; Inhibition of Neutrophil Elastase Suppresses the Development of Skin Tumors in Hairless Mice; Journal of Investigative Dermatology, (1996), vol. 107:159–163.

Hendrix, Mary J.C., et al; Expression of Type IV Collagenase Correlates with the Invasion of Human Lymphoblastoid Cells Lines and Pathogenesis in SCID Mice; Molecular and Cellular Probes (1992) 6, 59–65.

De Marre, Anne, et al; Synthesis and Evaluation of Macromolecular Prodrugs of Mitomycin C; Journal of Controlled Release 36 (1995) 87–97.

Fidler, Isaiah J.; Critical Factors in the Biology of Human Cancer Metastasis: Twenty Eight G.H.A. Clowes Memorial Award Lecture, Cancer Research 50, 6130–6138, Oct. 1, 1990.

McGuire, W, et.al., The New England Journal of Medicine, vol. 320, No. 8, pp 525–527 1989.

D. Theodorescu, et al; Dominance of Metastatically Competent Cells in Primary Murine Breast Neoplasms is Necessary for Distant Metastatic Spread, Int. J. Cancer; 47, 118–123, (1991).

Saiki, Ikuo; Antiadhesion Peptides in the Prevention of Tumour Metastasis, Disease Treatment Review, Clin. Immunother.1 (4) 1994 307–318.

* cited by examiner

Primary Examiner—Jon Weber
Assistant Examiner—Chih-Min Kam
(74) Attorney, Agent, or Firm—Michael P. Morris; Anthony P. Bottino; Timothy X. Witkowski

(57) ABSTRACT

Disclosed are enzyme-activated anti-tumor and anti-metastatic prodrug compounds. The specific enzymes are collagenase(IV) and elastase. Also disclosed are methods of making and using such compounds.

6 Claims, No Drawings

SEQUENCE LISTING

```
<160> NUMBER OF SEQ ID NOS: 16

<210> SEQ ID NO 1
<211> LENGTH: 5
<212> TYPE: PRT
<213> ORGANISM: Human
<220> FEATURE:
<221> NAME/KEY: MISC_FEATURE
```

```
<222> LOCATION: (1)..(1)
<223> OTHER INFORMATION: Amino acid 1 is Xaa wherein Xaa = a peptide
      amino capping group.
<220> FEATURE:
<221> NAME/KEY: MISC_FEATURE
<222> LOCATION: (1)..(5)
<223> OTHER INFORMATION: Targeting-peptide for elastase

<400> SEQUENCE: 1

Xaa Ala Ala Pro Val
1               5

<210> SEQ ID NO 2
<211> LENGTH: 5
<212> TYPE: PRT
<213> ORGANISM: Human
<220> FEATURE:
<221> NAME/KEY: MISC_FEATURE
<222> LOCATION: (1)..(1)
<223> OTHER INFORMATION: Amino acid 1 is Xaa wherein Xaa = a peptide
      amino capping group.
<220> FEATURE:
<221> NAME/KEY: MISC_FEATURE
<222> LOCATION: (1)..(5)
<223> OTHER INFORMATION: Targeting-peptide for elastase
<220> FEATURE:
<221> NAME/KEY: MISC_FEATURE
<222> LOCATION: (5)..(5)
<223> OTHER INFORMATION: Amino acid 5 is Xaa wherein Xaa = Nva which is
      norvaline.

<400> SEQUENCE: 2

Xaa Ala Ala Pro Xaa
1               5

<210> SEQ ID NO 3
<211> LENGTH: 5
<212> TYPE: PRT
<213> ORGANISM: Human
<220> FEATURE:
<221> NAME/KEY: MISC_FEATURE
<222> LOCATION: (1)..(5)
<223> OTHER INFORMATION: Adhesion peptide
<300> PUBLICATION INFORMATION:
<301> AUTHORS: Saiki
<303> JOURNAL: Clin. Immunother.
<304> VOLUME: 1
<305> ISSUE: 4
<306> PAGES: 307-318
<307> DATE: 1994

<400> SEQUENCE: 3

Tyr Ile Gly Ser Arg
1               5

<210> SEQ ID NO 4
<211> LENGTH: 5
<212> TYPE: PRT
<213> ORGANISM: Human
<220> FEATURE:
<221> NAME/KEY: MISC_FEATURE
<222> LOCATION: (1)..(5)
<223> OTHER INFORMATION: Adhesion peptide

<400> SEQUENCE: 4

Gly Arg Gly Asp Ser
1               5

<210> SEQ ID NO 5
<211> LENGTH: 4
<212> TYPE: PRT
```

```
<213> ORGANISM: Human
<220> FEATURE:
<221> NAME/KEY: MISC_FEATURE
<222> LOCATION: (1)..(4)
<223> OTHER INFORMATION: Targeting-peptide for collagenase (IV)

<400> SEQUENCE: 5

Gly Phe Ala Leu
1

<210> SEQ ID NO 6
<211> LENGTH: 4
<212> TYPE: PRT
<213> ORGANISM: Human

<400> SEQUENCE: 6

Ala Ala Pro Val
1

<210> SEQ ID NO 7
<211> LENGTH: 4
<212> TYPE: PRT
<213> ORGANISM: Human
<220> FEATURE:
<221> NAME/KEY: MISC_FEATURE
<222> LOCATION: (4)..(4)
<223> OTHER INFORMATION: Amino acid 4 is Xaa wherein Xaa = Nva which is
      norvaline.

<400> SEQUENCE: 7

Ala Ala Pro Xaa
1

<210> SEQ ID NO 8
<211> LENGTH: 4
<212> TYPE: PRT
<213> ORGANISM: Artificial Sequence
<220> FEATURE:
<223> OTHER INFORMATION: collegenase (IV) targeting peptide.
<220> FEATURE:
<221> NAME/KEY: NP_BIND
<222> LOCATION: (1)..(1)
<223> OTHER INFORMATION:
<220> FEATURE:
<221> NAME/KEY: NP_BIND
<222> LOCATION: (4)..(4)
<223> OTHER INFORMATION:

<400> SEQUENCE: 8

Gly Phe Ala Leu
1

<210> SEQ ID NO 9
<211> LENGTH: 4
<212> TYPE: PRT
<213> ORGANISM: Artificial Sequence
<220> FEATURE:
<223> OTHER INFORMATION: colleganese (IV) targeting peptide.
<220> FEATURE:
<221> NAME/KEY: NP_BIND
<222> LOCATION: (1)..(1)
<223> OTHER INFORMATION:
<220> FEATURE:
<221> NAME/KEY: NP_BIND
<222> LOCATION: (4)..(4)
<223> OTHER INFORMATION:

<400> SEQUENCE: 9

Gly Phe Ala Leu
1
```

<210> SEQ ID NO 10
<211> LENGTH: 4
<212> TYPE: PRT
<213> ORGANISM: Artificial Sequence
<220> FEATURE:
<223> OTHER INFORMATION: collegenase (IV) targeting peptide.
<220> FEATURE:
<221> NAME/KEY: NP_BIND
<222> LOCATION: (1)..(1)
<223> OTHER INFORMATION:
<220> FEATURE:
<221> NAME/KEY: NP_BIND
<222> LOCATION: (4)..(4)
<223> OTHER INFORMATION:

<400> SEQUENCE: 10

Gly Phe Ala Leu
1

<210> SEQ ID NO 11
<211> LENGTH: 4
<212> TYPE: PRT
<213> ORGANISM: Artificial Sequence
<220> FEATURE:
<223> OTHER INFORMATION: collegenase (IV) targeting peptide.
<220> FEATURE:
<221> NAME/KEY: NP_BIND
<222> LOCATION: (1)..(1)
<223> OTHER INFORMATION: attached to Gly at position 1 is N-Cbz.
<220> FEATURE:
<221> NAME/KEY: NP_BIND
<222> LOCATION: (4)..(4)
<223> OTHER INFORMATION: attached to Leu at position 4 is PABC-Doxorubicin.

<400> SEQUENCE: 11

Gly Phe Ala Leu
1

<210> SEQ ID NO 12
<211> LENGTH: 4
<212> TYPE: PRT
<213> ORGANISM: Artificial Sequence
<220> FEATURE:
<223> OTHER INFORMATION: collegenase (IV) targeting peptide.
<220> FEATURE:
<221> NAME/KEY: NP_BIND
<222> LOCATION: (1)..(1)
<223> OTHER INFORMATION: attached to Gly at position 1 is N-Cbz.
<220> FEATURE:
<221> NAME/KEY: NP_BIND
<222> LOCATION: (4)..(4)
<223> OTHER INFORMATION: attached to Leu at position 4 is PAB-OH.

<400> SEQUENCE: 12

Gly Phe Ala Leu
1

<210> SEQ ID NO 13
<211> LENGTH: 4
<212> TYPE: PRT
<213> ORGANISM: Artificial Sequence
<220> FEATURE:
<223> OTHER INFORMATION: elastase targeting peptide.
<220> FEATURE:
<221> NAME/KEY: NP_BIND
<222> LOCATION: (1)..(1)
<223> OTHER INFORMATION: attached to Ala at position 1 is t-Boc.
<220> FEATURE:
<221> NAME/KEY: NP_BIND
<222> LOCATION: (4)..(4)
<223> OTHER INFORMATION: attached to Val at position 4 is Doxorubicin.

```
<400> SEQUENCE: 13

Ala Ala Pro Val
1

<210> SEQ ID NO 14
<211> LENGTH: 4
<212> TYPE: PRT
<213> ORGANISM: Artificial Sequence
<220> FEATURE:
<223> OTHER INFORMATION: elastase targeting peptide.
<220> FEATURE:
<221> NAME/KEY: NP_BIND
<222> LOCATION: (1)..(1)
<223> OTHER INFORMATION: attached to Ala at position 1 is Z.

<400> SEQUENCE: 14

Ala Ala Pro Val
1

<210> SEQ ID NO 15
<211> LENGTH: 4
<212> TYPE: PRT
<213> ORGANISM: Artificial Sequence
<220> FEATURE:
<223> OTHER INFORMATION: elastase targeting peptide.
<220> FEATURE:
<221> NAME/KEY: NP_BIND
<222> LOCATION: (1)..(1)
<223> OTHER INFORMATION: attached to Ala at position 1 is Z.
<220> FEATURE:
<221> NAME/KEY: NP_BIND
<222> LOCATION: (4)..(4)
<223> OTHER INFORMATION: attached to Val at position 4 is Doxorubicin.

<400> SEQUENCE: 15

Ala Ala Pro Val
1

<210> SEQ ID NO 16
<211> LENGTH: 4
<212> TYPE: PRT
<213> ORGANISM: Artificial Sequence
<220> FEATURE:
<223> OTHER INFORMATION: elastase targeting peptide.
<220> FEATURE:
<221> NAME/KEY: NP_BIND
<222> LOCATION: (1)..(1)
<223> OTHER INFORMATION: attached to Ala at position 1 is t-Boc.
<220> FEATURE:
<221> NAME/KEY: NP_BIND
<222> LOCATION: (4)..(4)
<223> OTHER INFORMATION: attached to Val at position 4 is OH.

<400> SEQUENCE: 16

Ala Ala Pro Val
1
```

ENZYME-ACTIVATED ANTI-TUMOR PRODRUG COMPOUNDS

PRIORITY DATA

This application is a divisional of U. S. application Ser. No. 09/551,147, filed Apr. 15, 2000, now abandoned, which claims the benefit of Provisional application Ser. No. 60/134,135, filed May 14, 1999.

FIELD OF INVENTION

The invention relates to prodrug compounds capable of targeting and delivering cytotoxic drugs to tumors and metastatic cells. The drugs are useful in the treatment of cancer.

BACKGROUND OF THE INVENTION

Although many drugs are known that kill cancer cells, there are apparently none that can eradicate solid tumors at doses that are not lethal to the patient. Metastatic tumors are even more difficult to treat. Therefore, there is an advantage in cancer treatment to target the drug specifically to the tumor or metastasis. In this way, side effects, which occur at sites away from the tumor, can be suppressed.

Targeting requires a means of creating a therapeutically effective amount of active drug locally at the tumor site and at the same time reducing systemic administration. One strategy is to mask the drug as an inactive prodrug that is unmasked by some special property of the target cells. Denmeade, S. R., et al. *Cancer Research* 58, 2537–2540 (1998).

It is metastasis, more than any other phenomenon, that makes cancer a killer. Tumors that do not metastasize are usually curable by surgery, but those that do have a generally poor prognosis, even with chemotherapy that is effective against cells of the primary. Thus drugs that can easily kill most of a $10^9$-cell primary tumor are ineffective against metastatic tissue of only 1000 cells. It has been indicated that long-term survival for phases 2 and 3 of breast carcinoma (positive lymph nodes) are <10% even with chemotherapy, whereas for phase 1 (no positive lymph nodes) survival is >70% (McGuire, *N.E.J.M.* 320, 525 (1989).), often with no chemotherapy.

Clearly, metastatic cells are not just bits of the primary tumor. Instead, they arise from a tiny subpopulation that has the special powers of breaking away, surviving during transit in a hostile environment, lodging somewhere, penetrating basement membrane into a safe haven, and attracting its own blood supply (Fidler, *Cancer Res.* 50, 6130 (1990); Kerbel, *Int. J. Cancer* 47, 118 (1991). Micrometastes are those which do not have angiogenesis, i.e., the capacity to have their own blood supply.

Metastases are known to secrete a variety of hydrolytic enzymes not normally secreted at noncancer sites for the purpose of penetrating basement membrane. Most prominent among these enzymes is Collagenase IV (Goldfarb, Sem. Thromb. *Hemostasis* 12, 294 (1986); Hendrix, Molec. *Cell. Probes* 6, 59 (1992), which is also secreted by primary tumor cells. Until recently, this enzyme was not used for targeting because of the lack of good small-molecule substrates, but recently it was reported that Gly-Phe-Ala-Leu linked to polymer was cleaved rapidly by this enzyme (De Marre, J. Controlled Release 36, 87 (1995).

Another enzyme recently implicated in tumor invasion is elastase. Starcher, *J. Invest. Derm.* (1996), 107, 159. Peptide motifs which this enzyme binds and cleaves include X-Ala-Ala-Pro-Val (SEQ ID NO: 1) or X-Ala-Ala-Pro-Nva-(SEQ ID NO:2) where X is a peptide amino capping group and Nva is norvaline.

A potential way to intensify the enzymatic unmasking of drug specifically by metastatic cells is to take advantage of their special property to binding to basement membrane. Two peptide motifs which these cells have been found to bind to be useful as an adhesion peptide are Tyr-Ile-Gly-Ser-Arg (SEQ ID NO:3) and Gly-Arg-Gly-Asp-Ser (SEQ ID NO:4). Saiki, Clin. Immunother. 1, 307 (1994).

Totally lacking in the art, are prodrugs and methods to prolong contact time of a cytotoxic compound specifically with metastasizing cells, affording more efficient hydrolysis.

SUMMARY OF THE INVENTION

It is therefore an object of the invention to provide a prodrug compound having one or more targeting-peptides optionally covalently capped by a terminal amino capping group Z; a linker group covalently attached to the targeting peptide at the carboxy terminus; and a cytotoxic drug covalently attached to the linker. The targeting-peptide is an amino acid sequence which is capable of being catalytically cleaved by the enzymes: collagenase(IV) and elastase; the linker group is a bond or a self-immolating linker and Z is an amino protecting group or a peptide.

It is another object of the present invention to provide a method of treatment of particular cancers using the prodrug compounds and processes of making such compounds described herein.

DESCRIPTION OF THE PREFERRED EMBODIMENTS

The present invention relates to enzyme-activated anti-tumor and anti-metastatic prodrug compounds and methods of using such compounds. Particularly, the present invention provides for an active drug to be released outside the cancer cells. The prodrug is capable of being cleaved by the selected enzyme being secreted by a stromal or cancer cell which thereby produces free cytotoxic drug in the local area of these cells. The cytotoxic drug chosen must be capable of entering intact cells easily by diffusion. The prodrug compound according to the invention comprising:

one or more targeting-peptides optionally covalently capped by a terminal amino capping group Z;

a linker group covalently attached to the targeting peptide at the carboxy terminus; and a cytotoxic drug covalently attached to the linker;

wherein:

the targeting-peptide is an amino acid sequence which is capable of being catalytically cleaved by enzymes selected from the group consisting of: collagenase(IV) and elastase;

the linker group is a bond or a self-immolating linker and Z is an amino protecting group or a peptide.

The prodrugs according to the invention are capable of being converted into drugs by the catalytic action of cell-surface and integral membrane enzymes specifically expressed and secreted at above normal levels by metastatic cells and tumor cells. The enzymes according to the present invention are collagenase(IV) secreted by metastatic cells, elastase secreted by tumor cells and lysosomal enzymes. The lysosomal enzymes are found on the surface of metastatic cells. Preferably, the drugs are cytotoxic compounds possessing anticancer activity under physiological conditions.

The prodrug according to the invention comprises a targeting-peptide recognized by any of the aforementioned enzymes within which is a cleavage site which is catalyzed by the enzyme; and a cytotoxic drug. The targeting peptide and cytotoxic drug are covalently attached by a linker group. The cleavage site is between the P1 site of the targeting-peptide and the cytotoxic compound, or linker molecule if present, such that upon hydrolysis, a free cytotoxic compound is yielded.

The cytotoxic drug in accordance with the present invention is any drug having anticancer activity and capable of diffusing into tumor cells. Examples of such drugs include, but are not limited to, doxorubicin, mitomycin, paclitaxel, camptothecin, vincristine, vinblastine, fluorouracil, methotrexate and the like. Further examples include antiangiogenic drugs such as TNP-470, thalidomide, squalamine and the like. Most preferred is doxorubicin (Dox).

The linker group, if not a bond, is a self-immolating linker. This type of linker molecule functions to produce free cytotoxic drug. When the targeting-peptide is enzymatically cleaved at its cleavage site, this produces free targeting peptide and linker-cytotoxic drug. The linker spontaneously becomes unstable and subsequently dissociates from the cytotoxic drug to yield the free drug. Such molecules which function as self-immolating linker groups will be apparent to those skilled in the art and include PABC (para-aminobenzyl carbamate), GABA and the like, preferably PABC.

The Z group is any group which functions as an amino protecting group, for example BOC, benzyloxycarbonyl or O-Succinyl where the oxygen is attached to H or a lower-alkyl group such as methyl. Z may also be a peptide which functions as an adhesion peptide by binding to the basement membrane, preferred adhesion peptides are Tyr-Ile-Gly-Ser-Arg (SEQ ID NO: 3) and Gly-Arg-Gly-Asp-Ser (SEQ ID NO: 4). When such adhesion peptide is present, there may also be a spacer group between Z and the targeting peptide for spatial orientation to improve the binding capacity of the targeting-peptide with the enzyme. Such spacer group will be apparent to those skilled in the art and can be any unreactive molecule or polymer, examples include a polyalkylene oxide, one or more amino acids or carbohydrates. Any of the above targeting peptides may be covalently attached to an adhesion peptide by well known condensation reactions to form an amide bond between the C-terminus of the adhesion peptide and the N-terminus of the targeting-peptide; or if a spacer molecule is used, appropriate condensation reactions which crosslink the adhesion peptide, spacer and targeting-peptide can be determined without undue experimentation by one of ordinary skill.

Preferred prodrug compounds of the invention are those possessing a targeting-peptide selected from: Gly-Phe-Ala-Leu (SEQ ID NO: 5), Ala-Ala-Pro-Val (SEQ ID NO: 6), Ala-Ala-Pro-Nva (SEQ ID NO: 7) and conservative substitution variants thereof.

More preferred prodrug compounds are those where the targeting-peptide are Ala-Ala-Pro-Val (SEQ ID NO:6) for elastase; Gly-Phe-Ala-Leu (SEQ ID NO: 7) for collagenase (IV), and their respective conservative substitution variants thereof.

Another aspect of the present invention are pharmaceutical compositions comprising a compound of the present invention and optionally one or more suitable and pharmaceutically acceptable excipients, as exemplified in Remington: the science and practice of pharmacy. 19th ed. Easton: Mack Publ., 1995, incorporated herein by reference. The pharmaceutical compositions may be formulated as solids or solutions. Solid formulations may be for oral administration or preparation of a solution before injection. Preferably, the pharmaceutical compositions of the invention are solutions for injection. They may be administered systemically, e.g. by intravenous injection, or topically, e.g. by direct injection into the tumor site. The dosage will be adjusted according to factors like body weight and health status of the patient, nature of the underlying disease, therapeutic window of the compound to be applied, and the like. It is within the knowledge of the expert to adjust dosage appropriately. For example, when the prodrug comprises doxorubicin (Dox) as the cytotoxic drug, a dosage of 1–20 mg Dox/Kg is preferred. Administration may be repeated at appropriate time intervals. Accordingly, a further aspect of the present invention is the use of a compound of the invention in the preparation of a pharmaceutical composition.

The prodrug compounds of the invention are useful for the treatment of cancerous tumors and metastatic tumors. The prodrug compounds are especially useful for treatment of tumors which secrete the enzymes collagenase(IV) and elastase. The metastatic tumors are those which are associated with the enzymes collagenase(IV) and elastase and which are generally susceptible to chemotherapy. Tumors with this property are, for example, epithelial cancers and bone and soft tissue sarcomas. Thus, another aspect of the invention is a method of treatment of cancer, comprising administering a therapeutically effective amount of a prodrug of the invention to a patient in need thereof. The types of cancers include: breast carcinoma, pulmonary metastases, melanoma, sarcomas and liver, colorectal, prostate, testicular, ovarian, brain and bone cancer. See Saiki, I., *Clin. Immunother.* 1(4): 307–318 (1994); *Comprehensive Textbook of Oncology*, Vol.1 $2^{nd}$ Ed., 131–137.

"Amino acid residue" in the context of the present invention shall refer to any D or L naturally occurring or synthetic amino acid, preferably L or combinations of D and L depending on serum stability. Examples include: Gly, Ala, Val, Leu, Ile, Phe, Tyr, Trp, Cys, Met, Ser, Thr, Lys, Arg, His, Asp, Glu, Asn, Gln, Pro, trans-4-hydroxy-L-Pro, 5-hydroxy-L-Lys, norvaline , etc.

"Conservative substitution variants" in the context of the present invention shall refer a substitution of any D or L naturally occurring or synthetic amino acid for another of like charge. One example would be a substitution of a basic amino acid for another basic amino acid, i.e., Arg for His. Other examples of conservative substitutions will be apparent to those skilled in the art.

In the context of this invention, a "drug" shall mean a chemical compound that may be administered to humans or animals as an aid in the treatment of disease. In particular, a drug is an active pharmacological agent.

The term "cytotoxic compound" or "cytotoxic drug" shall mean a chemical compound which is toxic to living cells, in particular a drug that selectively kills dividing cells.

A "prodrug" shall mean a compound that, on administration, must undergo chemical conversion by metabolic processes before becoming an active pharmacological agent. In particular, a prodrug is a precursor of a drug. In the context of the present invention, the prodrug is significantly less cytotoxic than the drug it is converted into upon the catalytic action of the enzymes collegenase(IV) and elastase. The expert knows methods of determining cytotoxicity of a compound. Reference in this regard may be made to Mosmann (1983) *J. Immun. Meth.* 65, 55–63. Preferably, as the ordinary artisan would appreciate, the prodrug is at least several times less cytotoxic as compared to the drug in an in vitro assay.

A "drug being cytotoxic under physiological conditions" shall mean a chemical compound which is cytotoxic in a living human or animal body, in particular a compound that selectively kills dividing cells within a living human or animal body.

A "an amino acid sequence capable of being catalytically cleaved by enzymes" shall mean a prodrug which can act as a substrate for the enzymatic activity of the enzymes according to the invention. In particular, the enzymatic activity of the enzymes collegenase(IV) and/or elastase can catalyse cleavage of a covalent bond of the prodrug under physiological conditions. By cleavage of this covalent bond, the prodrug is converted into the drug. The enzymatic activity being the expression product of cells associated with tumor tissue. The enzymatic activity on the cleavage site of the targeting peptide converts the prodrug to a free cytotoxic drug free of targeting peptide and linking group. Most preferably, the cleavage site is specifically recognised by the enzymes according to the invention, but not by other proteolytic enzymes present in the human or animal body. That is, the cleavage site must be specific for the enzymes according to the invention. In a preferred embodiment, the cleavage site comprises a L-amino acid residue which is linked to a cytotoxic drug via a linking group. Another preferred embodiment is a doxorubicin-peptide conjugate. The enzymes collegenase(IV) and elastase each may catalyse the cleavage of a specific peptidic bond between the C-terminal amino acid residue of the specific peptide and the cytotoxic compound.

GENERAL METHOD OF SYNTHESIS

The compounds of the invention may be produced by the following general process which, while indicating particular embodiments of the invention, is not intended to be limiting to such embodiments. All starting materials, such as N-Cbz-Gly-Phe-OH, can be made be methods known to one of ordinary skill in the art. As will be appreciated by the skilled artisan, the peptides in the schemes below can be substituted with any appropriate peptide possessing a free hydroxy group, and under suitable conditions, be covalently attached by known methods to the desired cytotoxic drug.

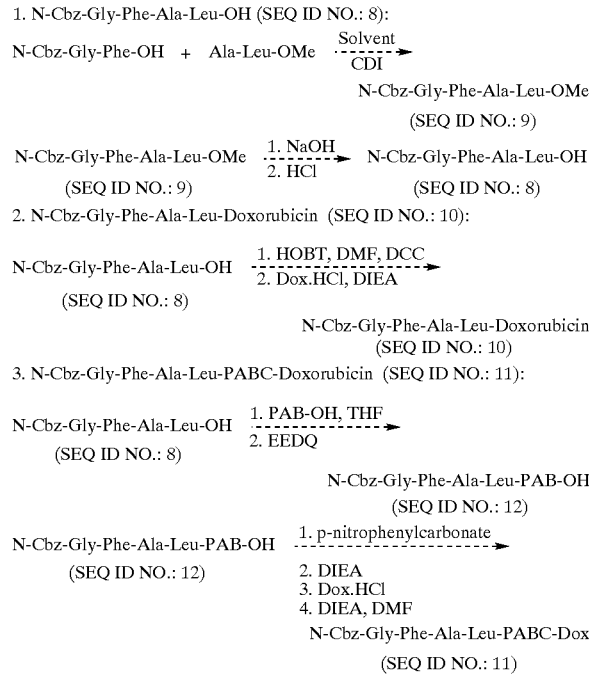

Scheme A
Synthesis of collegenase (IV) targeting peptides:

Scheme B
Synthesis of elastase targeting peptides:

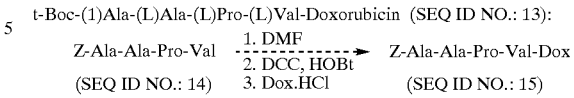

In order that this invention be more fully understood, the following examples are set forth. These examples are for the purpose of illustrating preferred embodiments of this invention, and are not to be construed as limiting the scope of the invention in any way.

EXAMPLES

Synthetic Procedures of Doxorubicin Conjugates

I. Synthetic Procedures of Doxorubicin Conjugates for Collagenase IV:

Example 1

N-Cbz-Gly-Phe-Ala-Leu-OH (SEQ ID NO: 8): N-Cbz-Gly-Phe-OH (5.0 g, 0.0057 mol) was dissolved in THF (60 ml) in a 250 ml round bottom flask. Under positive dinitrogen pressure, carbonyldiimidaZole (2.55 g, 0.0057 mol) was added at once. The solution was stirred 40 minutes at room temperature. Ala-Leu-OMe.HCl (4 g, 0.057 mol) was weighed out in a separate vial and dissolved in 5 ml of THF. N,N-Diisopropylethylamine, (2.73 ml, 0.057 g) was added and the resulting viscous oil was added to the first flask via syringe. Mild warming and a greenish blue color was noted. The flask was stirred for 24 hours, after which it was quenched with 10% citric acid and the product extracted with ethyl acetate. The ethyl acetate was removed in vacuo and N-Cbz-Gly-Phe-Ala-Leu-OMe (SEQ ID NO.: 9) (7.2 g) was isolated as a white solid.

The methyl ester was dissolved in methanol (20 ml) and isopropanol (30 ml) and placed in an ambient temperature bath. A solution of 1 M NaOH (12 ml) was added, and the reaction was stirred for 3 hours. When no more starting material was apparent by TLC, the solution was acidified with 1 M HCl (10 ml) and the organic solvents were removed in vacuo. The remaining concentrated aqueous solution was further acidified with an additional 2 ml of 1 M HCl, and placed in a refrigerator (4° C.) over night to crystallize. A white solid was isolated and used without further purification.

Example 2

N-Cbz-Gly-Phe-Ala-Leu-Doxorubicin (SEQ ID NO.: 10): N-Cbz-Gly-Phe Ala-Leu-OH (SEQ ID NO.: 8) (204 mg, 0.377 mmol) was weighed out and placed in a 100 ml round bottom flask. N-hydroxybenzotriazole (HOBT) (51 mg, 0.378 mmol) was added followed by DMF (10 ml). Dicyclohexylcarbodiimide (78 mg, 0.378 mmol) was weighed into a separate vial, dissolved in DMF (10 ml) and added to the solution, which was then stirred for 20 minutes at room temperature.

Into another separate vial, doxorubicin HCl (100 mg, 0.172 mmol) and N,N-diisopropylethylamine (33 µl, 0.378 mmol) were dissolved and added via syringe to the peptide solution. The resulting solution was stirred overnight at room temperature. The reaction mixture was quenched with 10% citric acid solution and the product was extracted with diethyl ether (11). The diethyl ether was washed with saturated aqueous sodium bicarbonate (250 ml) and brine (500 ml). The organic extract was dried with anhydrous MgSO$_4$ and the ether was removed in vacuo. The product, which was rich in DMF contaminant, was chromatographed on a C-18 reversed phase column with 8:2 methanol:water as the eluent. One orange spot, rf≈0.3, which fluoresced under long wave UV light, was isolated. The methanol was removed in vacuo to give a red amorphous solid.

Example 3

N-Cbz-Gly-Phe-Ala-Leu-PABC-Doxorubicin (SEQ ID NO.: 11): N-Cbz-Phe-Ala-Leu-OH (3 g, 5.5 mmol) and p-aminobenzyl alcohol [PABOH] (0.684 g, 5.5 mmol) were weighed out and placed in a 100 ml 2 neck round bottom flask equipped with a stir bar. THF (25 ml) was added with stirring followed by EEDQ [1-ethyloxycarbonyl-2-ethyloxy-1,2-dihydroquinoline] (1.37 g, 5.5 mmol). The reaction was quenched with 10% citric acid solution and the product was extracted with ethyl acetate.

The ethyl acetate layer was dried with $MgSO_4$ and the solvent removed in vacuo. An amorphous white solid was isolated and used without further purification.

A scoop of molecular sieves were activated in the microwave, allowed to cool in vacuo, then placed under a nitrogen atmosphere. N-Cbz-Phe-Ala-Leu-PABOH (220 mg, 0.34 mmol) and p-nitrophenylcarbonate (150 mg, 0.49 mmol) were weighed out and added to the sieves under positive nitrogen pressure. Methylene chloride (40 ml) was added to the flask followed by N, N-diisopropylethylamine (100 μl, 1.1 mmol). A yellow green color was immediately apparent. The solution was stirred overnight. The molecular sieves were filtered away and as much solvent as practically possible was removed under the reduced pressure of the filtration apparatus.

In a separate flask, doxorubicin HCl (100 mg, mmol), N, N-diisopropylethylamine (100 μl, 1.1 mmol), and DMF (35 ml) were stirred under a nitrogen atmosphere. The residue from the first filtration, which was a concentrated liquid, was added via syringe. The resulting solution was stirred overnight.

The reaction was then quenched with 10% citric acid and extracted with ethyl acetate (2 l). The ethyl acetate layer was dried with $MgSO_4$ and the solvent was removed in vacuo. The resulting DMF-rich red oil was chromatographed on a C-18 reversed phase silica column with 7:3 MeOH $H_2O$ as the eluent. One orange spot, rf≈0.3, which fluoresced under long wave UY light, was isolated. The methanol and water were removed in vacuo to give a red amorphous solid.

II. Synthetic Procedures of Doxorubicin Conjugates for Elastase:

Example 4 t-Boc-Ala-Ala-Pro-Val-Doxorubicin (SEQ ID NO.: 14):

t-Boc-AAPV-OH (SEQ ID NO.: 16) was dissolved in DMF (Aldrich, 20 mL). Dicyclohexylcarbodiimide (Aldrich, 72 mg, 0.35 mmol) and 1-hydroxybenzotriazole (Aldrich, 50 mg, 0.37 mmol) were added. Doxorubicin HCl (Meiji Seika Pharma Int. Ltd., CDXB 20412, 111 mg, 0.19 mmol) dissolved in a small amount of DMF was added. The red reaction mixture was stirred at ambient temperature for 72 hours. The solution was evaporated to dryness and chromatographed on a $C_{18}$ reverse-phase silica-gel column (EM Scientific) using methanol-water (80:20, 10 mL fractions). The product was found in fractions 8–14 which were combined and evaporated and lyophilized to give 98.6 mg (53% yield) of a TLC homogeneous red powdery product. $^1H$ NMR (400 MHz): 14.1 (s), 13.3 (s), 7.9 (d), 7.7 (m), 7.5 (d), 6.9 (d), 5.6 (d), 5.4 (s), 5.2 (s), 4.9 (br s), 4.8 (br s), 4.7 (br d), 4.6 (d), 4.5 (m), 4.4 (m), 4.2 (m), 4.1 (m) 4.0 (s and m), 3.5 (m) 3.0 (ab q), 2.3–0.8 (br m).

Measurement of Cleavage of Doxorubicin-peptide Conjugates

Samples are to be separated by reversed-phase high performance liquid chromatographic (HPLC) assay that is established to measure cleavage of doxorubicin-peptide conjugates. The HPLC system consists of a Waters 717 autosampler equipped with a 100 microliter (ul) loop and two Waters model 510 pumps to deliver solvents. Separations can be performed under isocratic conditions at a flow rate of 0.7 ml/min on a Nucleosil C-18 column, 100×4 mm I.D. with 5 um particle size. The mobile phase consists of methanol:water (70:30, v/v) containing 0.2 M ammonium acetate, adjusted to pH 3.2. Free doxorubicin and doxorubicin-peptide conjugates can be detected by fluorescence (excitation, 475 nm; emission, 585 nm) using a Waters 474 fluorescence detector. Injection, solvent delivery, data acquisition, and data analysis are all performed using the Millennium 2010 chromatography software package (Waters Corp., Milford, Mass., USA). Substances to be tested are first dissolved in dimethyl sulfoxide at a concentration of 5 mM and subsequently diluted in aqueous solution before being applied to the HPLC column.

In analyzing the ability of soluble enzyme to release free doxorubicin from doxorubicin-peptide conjugates: doxorubicin-peptide conjugate stock solutions (5 mM) are diluted with Hepes-buffered saline pH 7.4 to a final concentration of 50 to 100 uM. About 20 ul of the resulting solution is to be mixed with about 50 ul of purified enzyme or a fusion protein of the enzyme (approximately 20 ng) described above and 30 ul Hepes-buffered saline, pH 7.4. The mixture should incubate at 37° C. for 1 day and release of free doxorubicin is measured in the HPLC assay described. Areas under each peak are quantified using the software package above and the initial value is set to 100%. The rate of release of free doxorubicin is measured by the appearance of a peak with the same retention time as free doxorubicin under these HPLC conditions. The areas under each peak is used to calculate the relative amounts of free doxorubicin to doxorubicin-peptide conjugate.

All references cited in this application are incorporated in their entirety by reference.

What is claimed is:

1. A prodrug compound comprising:
   a targeting-peptide chosen from SEQ ID NO:6 or SEQ ID NO:7, wherein the targeting-peptide has L or L and D amino acid residues and wherein the targeting-peptide is optionally covalently capped by a terminal amino capping group Z;
   a linker group covalently attached to the targeting-peptide at the carboxy terminus; and
   a cytotoxic drug covalently attached to the linker; wherein:
   the targeting-peptide is an amino acid sequence which is catalytically cleaved by elastase;
   the linker group is a bond or a self-immolating linker; and
   Z is an amino protecting group chosen from tert-butyloxycarbonyl, benzyloxycarbonyl or an adhesion peptide; wherein there is an optional spacer molecule between Z and the targeting-peptide.

2. The prodrug compound according to claim 1 wherein the cytotoxic drug is selected from doxorubicin, mitomycin, paclitaxel, camptothecin, vincristine, vinblastine, fluorouracil, methotrexate, TNP-470, thalidomide and squalamine.

3. The prodrug compound according to claim 2 wherein the cytotoxic compound is doxorubicin.

4. The prodrug compound according to claim 3 wherein there is a spacer molecule between Z and the targeting-peptide.

5. The prodrug compound according to claim 4 wherein Z is an adhesion peptide selected from SEQ ID NO:3 and SEQ ID NO:4, wherein Z has L or L and D amino acid residues.

6. A pharmaceutical composition comprising a therapeutically effective amount of a prodrug compound according to claim 1.

* * * * *